United States Patent
Rapacki et al.

(10) Patent No.: US 7,036,509 B2
(45) Date of Patent: May 2, 2006

(54) MULTIPLE SEAL PORT ANESTHESIA ADAPTER

(75) Inventors: Alan R. Rapacki, Redwood City, CA (US); Michael Barrett, Campbell, CA (US); Michael J. Hendricksen, Redwood City, CA (US); Ronald R. Hundertmark, San Mateo, CA (US)

(73) Assignee: Emphasys Medical, Inc., Redwood City, CA (US)

( * ) Notice: Subject to any disclaimer, the term of this patent is extended or adjusted under 35 U.S.C. 154(b) by 0 days.

(21) Appl. No.: 11/004,560

(22) Filed: Dec. 3, 2004

(65) Prior Publication Data

US 2005/0161048 A1 Jul. 28, 2005

Related U.S. Application Data

(60) Provisional application No. 60/527,478, filed on Dec. 4, 2003.

(51) Int. Cl.
*A61M 16/00* (2006.01)
*A62B 9/04* (2006.01)

(52) U.S. Cl. .............................. 128/207.14; 128/202.27

(58) Field of Classification Search ........... 128/200.24, 128/202.27, 203.11, 203.22, 207.14, 207.15, 128/207.16, 207.17, 912, 200.26, DIG. 26; 604/533, 534, 538, 539; 137/849
See application file for complete search history.

(56) References Cited

U.S. PATENT DOCUMENTS

| | | | | |
|---|---|---|---|---|
| 4,489,721 A | * | 12/1984 | Ozaki et al. ............. | 128/205.24 |
| 4,674,496 A | * | 6/1987 | Svadjian et al. ........ | 128/207.16 |
| 4,848,331 A | * | 7/1989 | Northway-Meyer ... | 128/200.26 |
| 5,000,745 A | * | 3/1991 | Guest et al. ............... | 604/256 |
| 5,009,391 A | * | 4/1991 | Steigerwald ............. | 251/149.1 |
| 5,176,652 A | * | 1/1993 | Littrell ................... | 604/167.04 |
| 5,389,081 A | * | 2/1995 | Castro .................... | 604/167.03 |
| 5,735,271 A | | 4/1998 | Lorenzen et al. ...... | 128/207.16 |
| 5,954,766 A | | 9/1999 | Zadno-Azizi et al. ...... | 623/1.24 |
| 6,062,217 A | * | 5/2000 | Gray ...................... | 128/205.13 |
| 6,086,529 A | * | 7/2000 | Arndt ......................... | 600/114 |
| 6,382,255 B1 | * | 5/2002 | McFarland ................. | 137/849 |
| 6,569,120 B1 | * | 5/2003 | Green et al. ........... | 604/167.04 |
| 6,615,835 B1 | * | 9/2003 | Cise et al. ............. | 128/207.14 |
| 6,629,530 B1 | * | 10/2003 | Cise ...................... | 128/205.24 |
| 6,632,243 B1 | | 10/2003 | Zadno-Azizi et al. ...... | 623/1.24 |
| 6,679,264 B1 | | 1/2004 | Deem et al. ........... | 128/207.16 |
| 6,694,979 B1 | | 2/2004 | Deem et al. ........... | 128/207.14 |

(Continued)

FOREIGN PATENT DOCUMENTS

WO 01/66190 9/2001

(Continued)

*Primary Examiner*—Teena Mitchell
(74) *Attorney, Agent, or Firm*—Fish & Richardson P.C.; Fred C. Hernandez

(57) ABSTRACT

Disclosed is an anesthesia adapter that is suitable for the simultaneous insertion of multiple devices or instruments into the lungs during ventilation of the patient, while minimizing or eliminating gas leaks. The anesthesia adapter comprises in one embodiment a first port sized to receive a first elongate instrument; a second port sized to receive a second elongate instrument; an endotrachial tube fitting configured to be coupled to an endotrachial tube, the endotrachial tube fitting fluidly coupled to the first and second ports; and a hose fitting configured to be coupled to a ventilator hose, the hose fitting fluidly coupled to the first and second ports. The first port seals around the first elongated instrument and the second port seals around the second elongate instrument.

4 Claims, 5 Drawing Sheets

U.S. PATENT DOCUMENTS

| | | | |
|---|---|---|---|
| 6,698,424 B1 * | 3/2004 | Madsen et al. | 128/202.27 |
| 6,840,243 B1 | 1/2005 | Deem et al. | 128/207.16 |
| 2002/0077696 A1 | 6/2002 | Zadno-Azizi et al. | 623/1.24 |
| 2002/0095209 A1 | 7/2002 | Zadno-Azizi et al. | 623/1.24 |
| 2003/0070682 A1 | 4/2003 | Wilson et al. | 128/207.16 |
| 2003/0070683 A1 | 4/2003 | Deem et al. | 128/207.16 |
| 2003/0075169 A1 | 4/2003 | Deem et al. | 128/200.19 |
| 2003/0075170 A1 | 4/2003 | Deem et al. | 128/200.19 |
| 2003/0127090 A1 | 7/2003 | Gifford et al. | 128/200.24 |
| 2003/0164168 A1 | 9/2003 | Shaw et al. | 128/200.24 |
| 2003/0188750 A1 * | 10/2003 | Christopher | 128/207.14 |
| 2003/0192550 A1 | 10/2003 | Deem et al. | 128/207.14 |
| 2003/0192551 A1 | 10/2003 | Deem et al. | 128/207.14 |
| 2003/0199972 A1 | 10/2003 | Zadno-Azizi et al. | 623/1.24 |
| 2003/0212452 A1 | 11/2003 | Zadno-Azizi et al. | 623/1.24 |
| 2003/0228344 A1 | 12/2003 | Field et al. | 424/423 |
| 2004/0016435 A1 | 1/2004 | Deem et al. | 128/207.14 |
| 2004/0039250 A1 | 2/2004 | Tholfsen et al. | 600/104 |
| 2004/0055606 A1 | 3/2004 | Hendricksen et al. | 128/207.14 |
| 2004/0060563 A1 | 4/2004 | Rapacki et al. | 128/207.14 |
| 2004/0074491 A1 | 4/2004 | Hendricksen et al. | 128/200.19 |
| 2004/0089306 A1 | 5/2004 | Hundertmark et al. | 128/207.14 |
| 2004/0134487 A1 | 7/2004 | Deem et al. | 128/200.19 |
| 2004/0148035 A1 | 7/2004 | Barrett et al. | 623/23.65 |
| 2004/0154621 A1 | 8/2004 | Deem et al. | 128/206.24 |
| 2005/0016530 A1 | 1/2005 | McCutcheon et al. | 128/200.24 |

FOREIGN PATENT DOCUMENTS

| | | |
|---|---|---|
| WO | 01/87170 | 11/2001 |
| WO | 03/030975 | 4/2003 |
| WO | 03/099164 | 4/2003 |
| WO | 03/041779 | 5/2003 |
| WO | 03/075796 | 9/2003 |
| WO | 2004/010845 | 2/2004 |
| WO | 2004/049974 | 6/2004 |
| WO | 2005/007023 | 1/2005 |

* cited by examiner

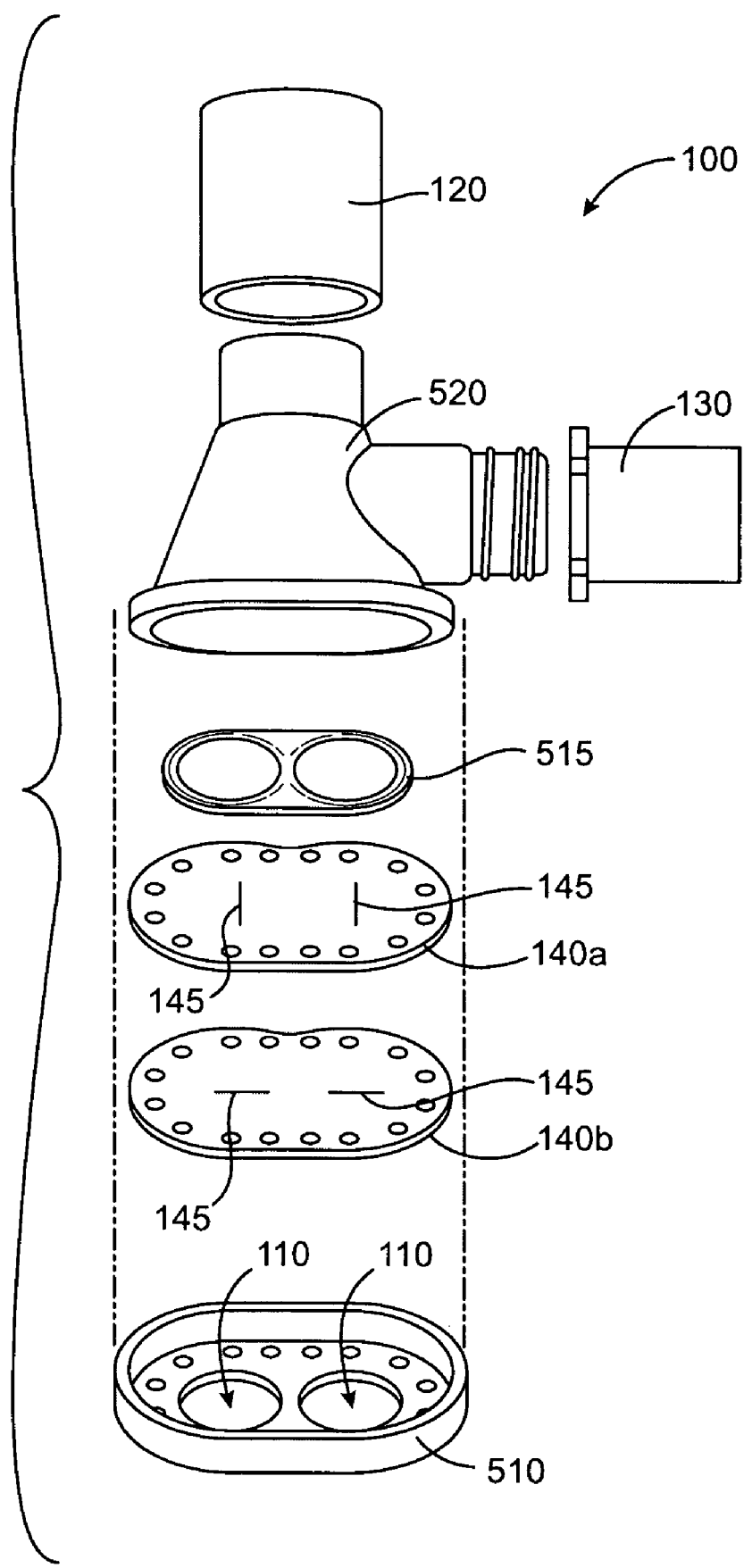

US 7,036,509 B2

MULTIPLE SEAL PORT ANESTHESIA ADAPTER

REFERENCE TO PRIORITY DOCUMENT

This application claims priority of co-pending U.S. Provisional Patent Application Ser. No. 60/527,478, entitled "Multiple Seal Port Anesthesia Adapter", filed Dec. 4, 2003. Priority of the aforementioned filing date is hereby claimed, and the disclosure of the Provisional Patent Application is hereby incorporated by reference in its entirety.

BACKGROUND

This disclosure relates generally to methods and devices for use in performing pulmonary procedures.

When a patient is ventilated in order to perform a surgical procedure, an endotracheal tube is inserted into the airway of the patient. An inflatable cuff or other sealing mechanism is actuated in order to seal the outside of the endotracheal tube to the airway of the patient to prevent air leaks around the tube. The proximal end of the endotracheal tube is connected to the ventilator, and the ventilator is turned on to begin breathing for the patient.

The ventilator performs the inhalation portion of the natural breathing cycle by actively pushing gas into the lungs through the endotracheal tube, and then allowing the natural elastic recoil of the lungs and the chest wall to force the gas out of the lungs during the exhalation portion of the breathing cycle. The physician operating the ventilator—typically the anesthesiologist—can adjust the breathing rate and the tidal volume (volume of gas pushed into the lungs during inhalation), as well as other parameters.

The ventilator can ventilate the patient with any of a variety of gases, such as room air, oxygen of varying concentrations, or when required, gaseous anesthetics such as isoflourane. No matter what gas is used to ventilate the patient, it is important that there are minimal or no gas leaks from the system during ventilation. If there are leaks, the patient is receiving a smaller tidal volume than intended, and if the gas used is an anesthetic, leaks will result in anesthetic gas entering the operating room and possibly affecting the medical staff.

In order to perform bronchoscopic procedures on a ventilated patient, it is necessary to have access to the airway for the bronchoscope and for other instruments and devices. This is desirably done in a way that minimizes or eliminates gas leaks. During a bronchoscopic procedure where the patient is ventilated, the bronchoscope may have to be inserted into and removed from the airway numerous times during the procedure. In order to facilitate this, there are currently anesthesia adapters available that are interposed between the hose leading from the ventilator and the proximal end of the endotracheal tube. These adapters typically contain a flexible elastomeric valve that allows the bronchoscope, usually lubricated with a surgical lubricant, to be inserted into the endotracheal tube (and thus the lungs) to perform a procedure in the lungs. The valve seals around the bronchoscope shaft to prevent gas leaks.

Once the bronchoscope is removed from the endotracheal tube, the anesthesia adapter valve can seal automatically to prevent gas leaks therefrom. Alternately, the anesthesia adapter valve can have a plug or other mechanism that may be manually applied by the operator to stop leaks.

Current anesthesia adapters are designed to allow just a single instrument, such as a bronchoscope, to be inserted into the lungs through the adapter, but are not designed to allow a second instrument or device to be inserted simultaneously. Procedures such as the implantation of bronchial isolation devices such as one-way valves or occluders, the implantation of tracheobronchial stents, etc. can often require at least two devices—such as both the bronchoscope and a delivery catheter, or the bronchoscope and a guidewire—to be inserted into the lungs simultaneously. Given that there a number of procedures that require the insertion of two devices or instruments through an anesthesia adapter into the lungs simultaneously, there is a need for an anesthesia adapter that can accommodate such procedures.

SUMMARY

Disclosed is an anesthesia adapter that is suitable for the simultaneous insertion of multiple devices or instruments into the lungs during ventilation of the patient, while minimizing or eliminating gas leaks. The anesthesia adapter comprises in one embodiment a first port sized to receive a first elongate instrument; a second port sized to receive a second elongate instrument; an endotrachial tube fitting configured to be coupled to an endotrachial tube, the endotrachial tube fitting fluidly coupled to the first and second ports; and a hose fitting configured to be coupled to a ventilator hose, the hose fitting fluidly coupled to the first and second ports. The first port seals around the first elongated instrument and the second port seals around the second elongate instrument.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 5 shows an exploded view of the anesthesia adapter.

DETAILED DESCRIPTION

Figure 1:
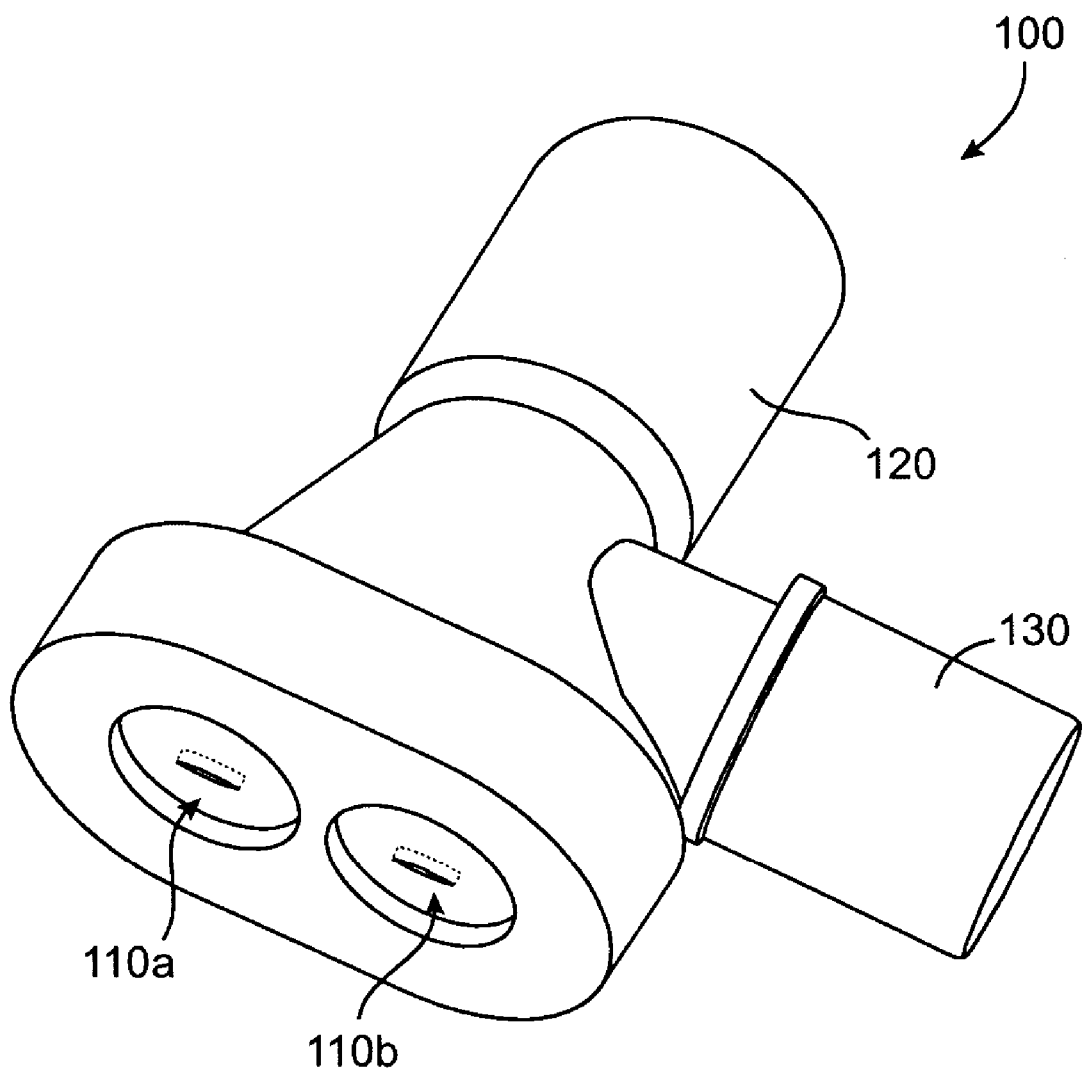
FIG. 1 shows a perspective view of a multi-port anesthesia adapter.

Described herein are anesthesia adapters that are suitable for the simultaneous insertion of multiple devices or instruments into the lungs during ventilation of the patient, while minimizing or eliminating gas leaks.

The multiple devices can be inserted through the anesthesia adapter and into the lungs pursuant to the treatment of lung diseases, such as, for example, emphysema. Some recently proposed treatments for emphysema or other lung ailments include the use of bronchial isolation devices that isolate a diseased region of the lung in order to modify the air flow to the targeted lung region or to achieve volume reduction or collapse of the targeted lung region. According to such treatments, one or more bronchial isolation devices are implanted in airways feeding the targeted region of the lung. The bronchial isolation device regulates fluid flow through the bronchial passageway in which the bronchial isolation device is implanted. The bronchial isolation devices can be, for example, one-way valves that allow flow in the exhalation direction only, occluders or plugs that prevent flow in either direction, or two-way valves that control flow in both directions.

The following references describe exemplary bronchial isolation devices: U.S. Pat. No. 5,954,766 entitled "Body Fluid Flow Control Device"; U.S. patent application Ser. No. 09/797,910, entitled "Methods and Devices for Use in Performing Pulmonary Procedures"; and U.S. patent application Ser. No. 10/270,792, entitled "Bronchial Flow Control Devices and Methods of Use". The foregoing references are all incorporated by reference in their entirety and are all assigned to Emphasys Medical, Inc., the assignee of the instant application.

One method of implanting bronchial isolation devices in the lung is through the use of a flexible guidewire and a delivery catheter with the bronchial isolation device releasably mounted to the distal end of the catheter. The catheter can have a central lumen running the length of the catheter that is sized so that a guidewire may slide freely through it. To implant the isolation device, a bronchoscope with a working channel large enough to allow the guidewire to slide freely through it is inserted into the trachea of a patient. The tip of the bronchoscope is navigated through the bronchial tree until it is proximal to the target device placement site. The guidewire is inserted into the entrance of the working channel in the handle of the bronchoscope and advanced until the distal tip of the guidewire emerges from the distal end of the bronchoscope and is placed across the implant site.

The bronchoscope is then removed from the patient while leaving the guidewire in place in a process called "guidewire exchange". The delivery catheter, with the bronchial isolation device compressed in the tip, is loaded over the proximal end of the guidewire and advanced down the guidewire and into the patient's lungs. The bronchoscope is inserted into the patient's lungs in parallel with the delivery catheter in order to visualize the delivery catheter as it slides down the guidewire to the target implant location. Once it has been visually confirmed that the distal end of the delivery catheter is in the target location, the catheter is activated and the device is delivered.

During this procedure, it can be necessary that both the bronchoscope and the delivery catheter be inserted into the patient's lung simultaneously. If this procedure is performed with the patient ventilated, both the bronchoscope and the delivery catheter must be allowed to move in and out of the patient's lungs freely while at the same time preventing gas leaks from the airway. Existing anesthesia adapters with a single instrument port or valve may be used for this; however, it is very difficult to fit both a bronchoscope and a delivery catheter through the single port at the same time, and gas leaks are common as the port or valve is designed for a single device or instrument.

In order to solve these difficulties, there is disclosed an improved anesthesia adapter that comprises at least some of the following features:

Two or more self-sealing ports for instruments or devices;
Minimal or no gas leaks under normal pressures found with positive pressure ventilators when an instrument is inserted into the port or when no instrument is present in the port;
Minimal friction or drag on the instrument or device when it is inserted through or removed from the port;
Easily connects to standard endotracheal tubes and ventilator supply hoses;
Durable enough to allow repeated insertions and removals of devices and instrument without a reduction in the gas sealing of the valves.

One embodiment of a device that includes the aforementioned features is shown in FIG. 1. With reference to FIG. 1, the device comprises an anesthesia adapter 100 that includes at least two instrument ports 110a and 110b comprised of openings. The instrument ports 110 each define an opening that can receive an elongated instrument, such as, for example a bronchoscope, guidewire, delivery catheters or the like. As described in more detail below, each port 110 has a seal member that seals around an instrument inserted through the port in order to prevent gas leaks between the instrument and the port. A separate seal member can be in each port 110a, 110b, or a single integrated seal member can be used for both ports 110a, 110b.

Figure 2:
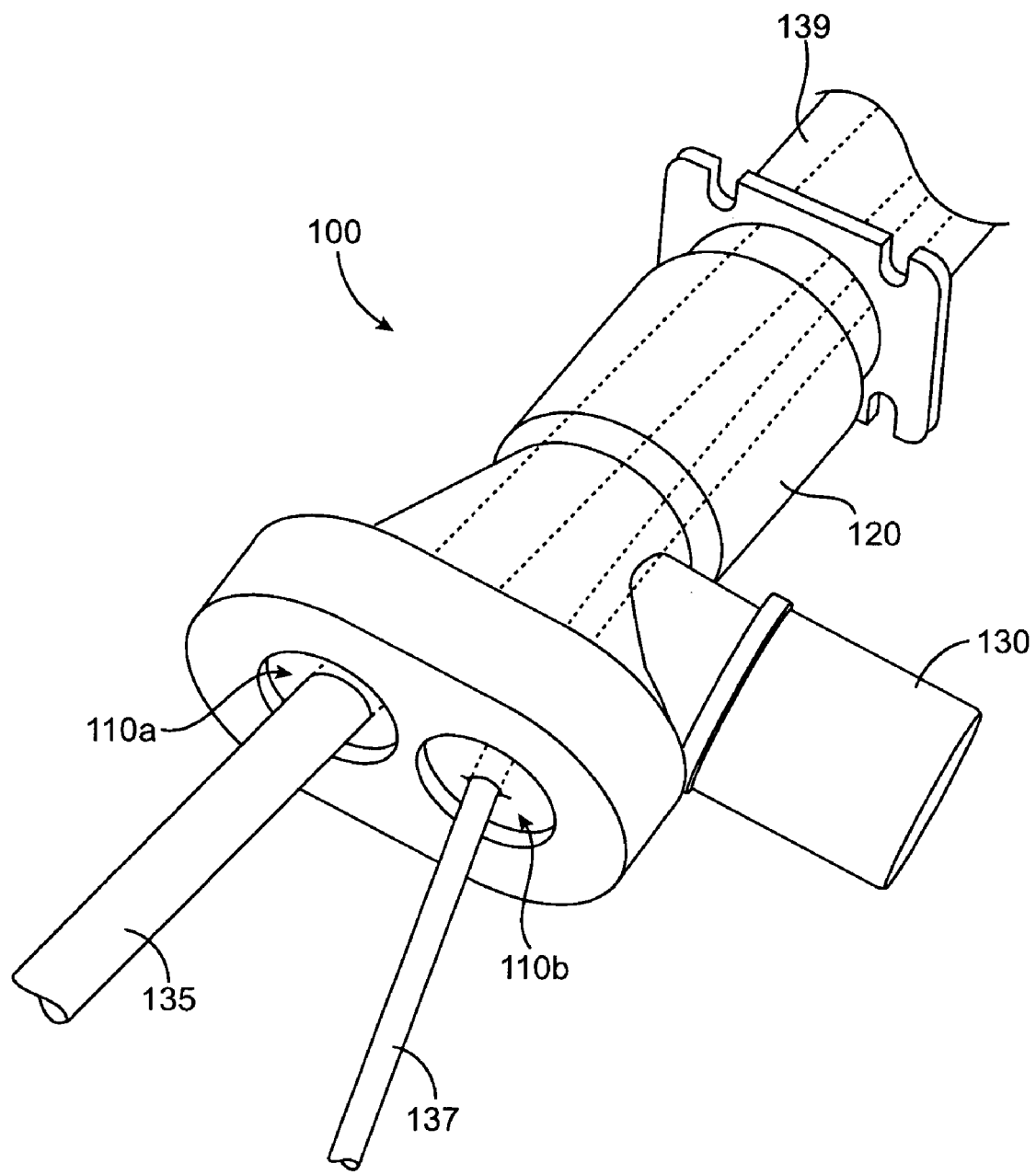
FIG. 2 shows the anesthesia adapter coupled to a bronchoscope, a delivery catheter, and an endotracheal tube.

The anesthesia adapter 100 also includes endotrachial tube fitting 120 configured to be coupled to an endotrachial tube (shown in FIG. 2). The anesthesia adapter 100 also includes a ventilator supply hose fitting 130 configured to be coupled to a ventilator supply hose. The fittings 120, 130 can have a variety of structures and can be male or female and can also be configured to swivel or rotate. The anesthesia adapter 100 is shown in FIG. 2 with a bronchoscope 135 and a delivery catheter 137 inserted into the ports 110a and 110b, respectively, and attached to an endotracheal tube 139.

Figure 3:
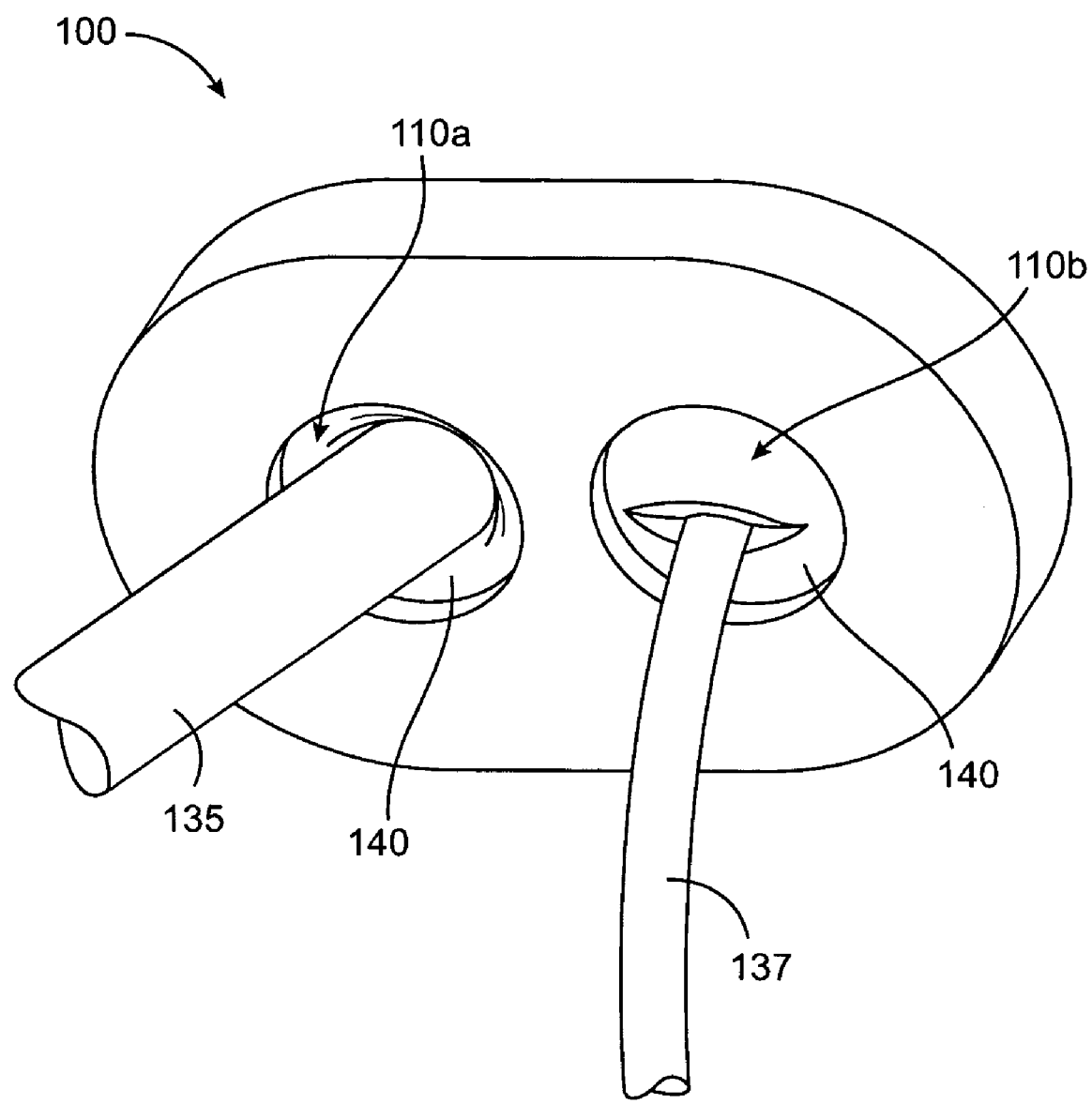
FIG. 3 shows a close-up view of the port regions of the anesthesia adapter with the bronchoscope and the delivery catheter inserted through respective ports.

In one embodiment, all components of the device are formed of injection molded thermoplastics; however, other materials and manufacturing methods are possible. The sealing ports 110 can be formed of two layers of a soft elastomer such as low durometer thermoplastic elastomer (TPE), such as, for example, around 30 Shore OO durometer. FIG. 3 shows a close-up view of the port regions of the anesthesia adapter 100 with the bronchoscope 135 and the delivery catheter 137 inserted through the ports 110a and 110b, respectively.

With reference to FIG. 3, at least one valve seal member 140 is disposed in each of the ports 110. A single valve seal member 140 can be used for both ports 110 or separate valve seal members 140 can be positioned in each port 110. The valve seal member 140 functions to seal around an instrument that is inserted through the port 110.

Figure 4:
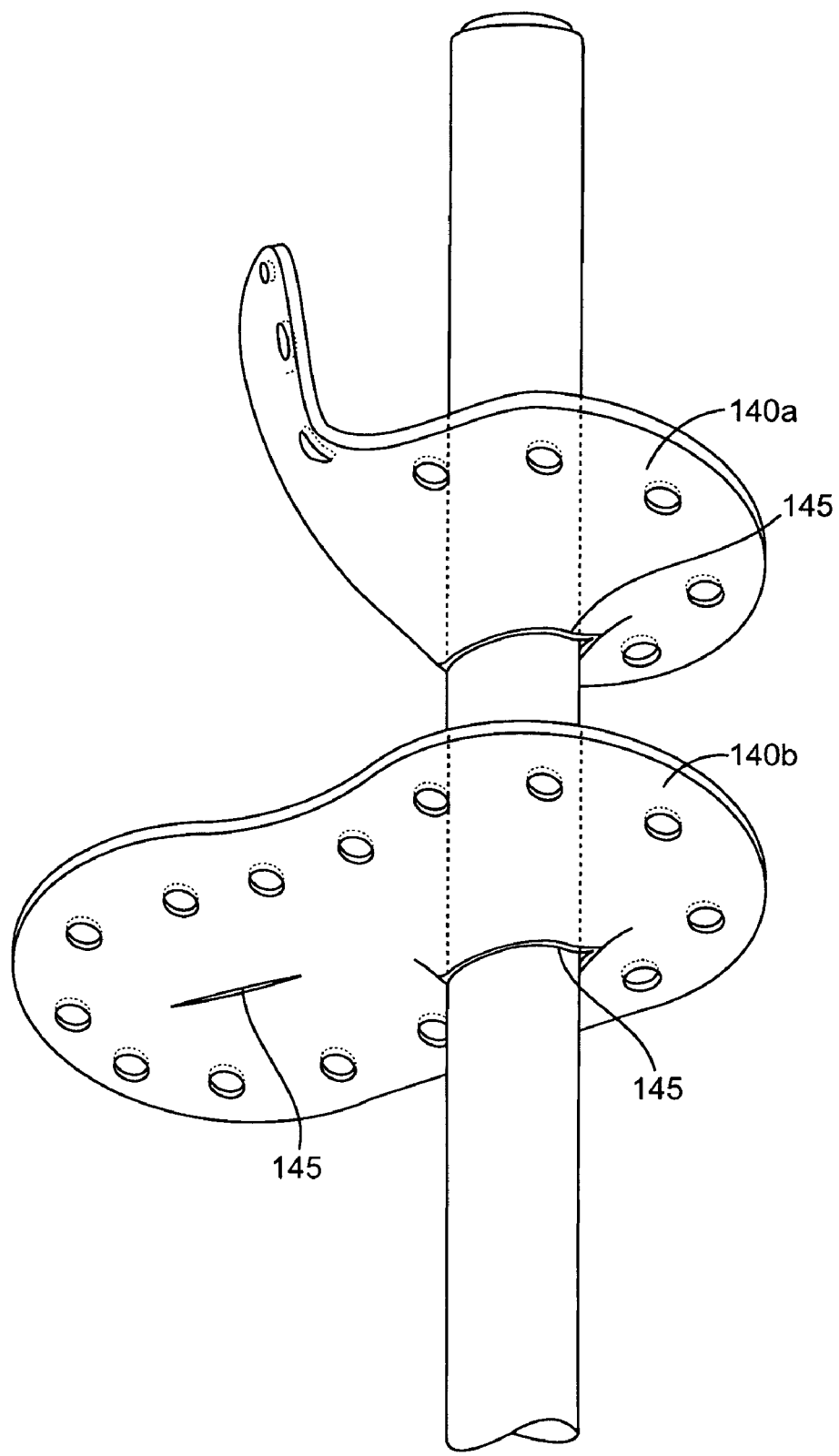
FIG. 4 shows an inner valve seal member and an outer valve seal member removed from the anesthesia adapter with a bronchoscope threaded through slits in the valve seals.

In one embodiment, the valve seal member 140 comprises a layer of soft material having at least one opening and that is configured to conform to the shape of an elongated instrument inserted through the opening. The opening can comprise, for example, a slit through which the instrument can be inserted. In one embodiment, the ports 110 each have two valve seal members that are juxtaposed with one another, including an inner valve seal member and an outer valve seal member. FIG. 4 shows an inner valve seal member 140a and an outer valve seal member 140b removed from the rest of the anesthesia adapter 110 and with a bronchoscope 135 threaded through slits in the valve seals. FIG. 4 shows the inner valve seal member 140a in a bent shape to illustrate the flexibility of the member. In the assembled anesthesia adapter 110, the valve seal members 140 are juxtaposed and positioned between a cap and a support plate, which are described below with reference to FIG. 5.

FIG. 5 shows an exploded view of the anesthesia adapter 100, which includes a cap 510, the outer seal 140b, the inner seal 140a, a support plate 515, and an adapter body 520. A supply hose fitting 130 is coupled to the adapter body 520 and an endotrachial tube fitting 120 is also coupled to the adapter body 520.

When the anesthesia adapter 100 is assembled, the valve seal members 140 are sandwiched next to each other between the cap 510 and the support plate 515, and the resulting assembly is coupled to the adapter body 520, such as in a snap-fit fashion. The cap 510 can have pins that engage holes in the outer and inner seal members 140 to facilitate alignment and to prevent the seals from being distorted when an instrument or device is inserted through the slits in the seals.

As mentioned, the valve seal members 140 can have openings, such as slits 145 for receiving therethrough the elongated instruments (such as the bronchoscope 135 and the delivery catheter 137). In one embodiment, the outer valve seal member 140b has a pair of slits centered with the corresponding pair of instrument ports 110. The inner valve seal member 140a also has a pair of slits centered on the corresponding pair of instrument ports 110. The slit(s) in the inner valve seal member 140a can be oriented transverse at an angle, such as at 90 degree angle, to the slit(s) in the outer valve seal member 140b, such as shown in FIG. 5.

When the instrument or device is inserted through one of the ports 110 in the anesthesia adapter 100, the slit 145 in the respective valve seal member 140 opens allowing the device to be inserted therethrough. The dual layer slits in the inner and outer valve seal members 140 form a tight gas seal around the device and prevent gas leaks. When the device is removed, the slits 145 close and form a tight seal without the instrument present through the slits. The multi-layered seals provide improved sealing capability over single-layered seals. A single-layer slit valve does provide some sealing around an inserted device or instrument, or when no instrument is present, and this design may be found in some existing anesthesia adapters. However, the double layer seal with the second slit oriented at a 90 degree angle to the slit in the first layer provides a far superior seal, both with and without instruments inserted. Single slit valves tend to leak at the corners of the slit, and the second layer of the valve seals this leak point. With a single layer valve, the seal may be improved by making the seal material extremely soft; however, this can reduce the ability of the valve to close and seal effectively after the removal of a previously inserted valve or instrument.

The sealing ability of single layer valves alternately may be improved by making the seals a very tight fit on the inserted instrument; however this means that the valve will seal only on a limited range of device or instrument diameters or sizes. The double layer valve allows a relatively soft material to be used for good sealing with an instrument inserted, while still maintaining good sealing with no instrument inserted. The second layer helps force the first slit to close once the instrument is removed.

It should be appreciated that other sealing port valve designs could be used such as flap valves, circular apertures, etc. In addition, three, four or more instrument ports are possible, as are other adapter shapes, designs and construction methods.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. An anesthesia adapter, comprising:
    an adapter body having a proximal end with an opening and a distal end with an opening, the distal end configured to be fluidly coupled to an endotracheal tube;
    a cap coupled to the proximal end of the adapter, the cap forming a first port sized to receive and seal around a first elongate instrument and a second port sized to receive and seal around a second elongate instrument; and
    a hose fitting having a first opening fluidly coupled to the adapter body and a second opening configured to be coupled to a ventilator hose;
    wherein the first and second ports are simultaneously aligned with the opening on the proximal end of the adapter, thereby providing simultaneous access to the endotracheal tube when the adapter body is coupled to the endotracheal tube.

2. The anesthesia adapter of claim 1, additionally comprising at least one outer valve seal member with an outer slit positioned in each of the first and second ports, wherein the outer slit in the first port is sized to receive the first elongate instrument and the outer slit in the second port is sized to receive the second elongate instrument.

3. The anesthesia adapter of claim 2, additionally comprising at least one inner valve seal member with an inner slit positioned in each of the first and second ports, the inner slit in the first port sized to receive the first elongate instrument and the inner slit in the second port sized to receive the second elongate instrument, wherein the inner slits are oriented transverse to the outer slits.

4. The anesthesia adapter of claim 3, wherein the inner slits are oriented at a ninety degree angle to the outer slits.

\* \* \* \* \*